(12) United States Patent
Pan et al.

(10) Patent No.: US 6,689,342 B1
(45) Date of Patent: Feb. 10, 2004

(54) ORAL CARE COMPOSITIONS COMPRISING TROPOLONE COMPOUNDS AND ESSENTIAL OILS AND METHODS OF USING THE SAME

(75) Inventors: Pauline Pan, Denville, NJ (US); Marybeth Finnegan, Hillsborough, NJ (US); Andre Soshinsky, Randolph, NJ (US); Georgia Arvanitis, Ewing, NJ (US); Michael Berardini, Ewing, NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/207,726

(22) Filed: Jul. 29, 2002

(51) Int. Cl.$^7$ .............................. A61K 7/16; A61K 7/26; A61K 9/68

(52) U.S. Cl. .............................. 424/49; 424/48; 424/58; 424/435; 424/440

(58) Field of Search ..................................... 424/49–88

(56) References Cited

U.S. PATENT DOCUMENTS

| | | | | |
|---|---|---|---|---|
| 2,770,545 | A | * 11/1956 | Thompson | 99/163 |
| 3,708,431 | A | * 1/1973 | Prussin | |
| 3,718,488 | A | * 2/1973 | Trofimenko et al. | 106/1 |
| 4,523,589 | A | 6/1985 | Krauser | |
| 4,656,192 | A | * 4/1987 | Yamato | 514/564 |
| 4,663,315 | A | 5/1987 | Hasegawa et al. | |
| 4,833,079 | A | * 5/1989 | Kamei et al. | 435/148 |
| 4,950,686 | A | * 8/1990 | Kondo et al. | 514/546 |
| 5,009,898 | A | 4/1991 | Sakuma et al. | |
| 5,594,144 | A | * 1/1997 | Itoh et al. | 548/166 |
| 5,645,845 | A | * 7/1997 | Neumann et al. | |
| 5,696,169 | A | 12/1997 | Otsu et al. | |
| 5,700,449 | A | * 12/1997 | Katayama et al. | |
| 5,703,071 | A | * 12/1997 | Itoh et al. | 514/218 |
| 5,939,050 | A | 8/1999 | Iyer et al. | |
| 5,990,160 | A | * 11/1999 | Islam et al. | 514/420 |
| 6,025,312 | A | 2/2000 | Saito et al. | |
| 6,048,836 | A | * 4/2000 | Romano et al. | |
| 6,096,328 | A | 8/2000 | Sagel et al. | |
| 6,228,833 | B1 | * 5/2001 | Paatz et al. | |
| 6,287,541 | B1 | * 9/2001 | Creeth et al. | |
| 6,310,255 | B1 | * 10/2001 | Nagato et al. | |

FOREIGN PATENT DOCUMENTS

| | | |
|---|---|---|
| EP | 900560 | 3/1999 |
| JP | 47043218 | 12/1972 |
| JP | 51023244 | 2/1976 |
| JP | 51033901 | 9/1976 |
| JP | 53099339 | 8/1978 |
| JP | 59175410 | 10/1984 |
| JP | 60016913 | 1/1985 |
| JP | 60116631 | 6/1985 |
| JP | 61100516 | 5/1986 |
| JP | 61286314 | 12/1986 |
| JP | 62181212 | 8/1987 |
| JP | 63005048 | 1/1988 |
| JP | 63188619 | 9/1988 |
| JP | 63211217 | 9/1988 |
| JP | 63211218 | 9/1988 |
| JP | 01305021 | 12/1989 |
| JP | 02027991 | 1/1990 |
| JP | 02069411 | 3/1990 |
| JP | 03000789 | 1/1991 |
| JP | 03115213 | 5/1991 |
| JP | 03151317 | 6/1991 |
| JP | 03193743 | 8/1991 |
| JP | 03271215 | 12/1991 |
| JP | 03279321 | 12/1991 |
| JP | 04198121 | 7/1992 |
| JP | 47043218 | 8/1993 |
| JP | 07133214 | 5/1995 |
| JP | 07187973 | 7/1995 |
| JP | 07187977 | 7/1995 |
| JP | 07233397 | 9/1995 |
| JP | 07258050 | 10/1995 |
| JP | 08003074 | 1/1996 |
| JP | 08040971 | 2/1996 |
| JP | 08183997 | 7/1996 |
| JP | 08193056 | 7/1996 |
| JP | 09188620 | 7/1997 |
| JP | 09188892 | 7/1997 |
| JP | 10182383 | 7/1998 |
| JP | 10194943 | 7/1998 |
| JP | 10212220 | 8/1998 |
| JP | 11001465 | 1/1999 |
| JP | 11012142 | 1/1999 |
| JP | 11060550 | 3/1999 |
| JP | 11130648 | 5/1999 |
| JP | 1158051 | 6/1999 |
| JP | 11158052 | 6/1999 |
| JP | 11197217 | 7/1999 |
| JP | 11222455 | 8/1999 |
| JP | 11228379 | 8/1999 |
| JP | 11256191 | 9/1999 |
| JP | 20000044422 | 2/2000 |
| KR | 98025533 | 1/1998 |
| WO | WO 98/44901 | 10/1998 |
| WO | WO 2000/016736 | 3/2000 |

* cited by examiner

*Primary Examiner*—Shep K. Rose
(74) *Attorney, Agent, or Firm*—Watov & Kipnes, P.C.

(57) ABSTRACT

The present invention relates to oral care compositions suitable for preventing or treating diseases or conditions of the oral cavity in warm-blooded animals including humans, comprising an oral care effective amount of at least one tropolone compound in combination with at least one essential oil, and a pharmaceutically acceptable oral carrier. This invention further relates to a method for preventing or treating diseases or conditions of the oral cavity in warm-blooded animals including humans, by applying an oral care effective amount of the oral care composition to the oral cavity.

21 Claims, No Drawings

ORAL CARE COMPOSITIONS COMPRISING TROPOLONE COMPOUNDS AND ESSENTIAL OILS AND METHODS OF USING THE SAME

FIELD OF THE INVENTION

The present invention is related generally to oral care compositions, more particularly to oral care compositions comprising substituted tropolone compounds and essential oils, and methods of using the same for oral care.

BACKGROUND OF THE INVENTION

Oral malodor, plaque, gingivitis, periodontal disease, and discoloration of the teeth, are all undesirable conditions that affect many people. First malodor of the oral cavity also known as halitosis or bad breath, has been broadly estimated to afflict 20 to 90 million individuals in the US. It is generally believed that the presence of anaerobic bacteria, especially gram-negative anaerobic bacteria, in the mouth contributes to this condition. Other oral conditions caused by microorganisms include periodontal disease, tooth decay, inflammation and the like.

Periodontal disease is a major cause of tooth loss in adults, and can manifest itself in people as young as age 12. Periodontal disease affects the periodontum, which is the investing and supporting tissues surrounding a tooth (i.e., the periodontal ligament, the gingiva, and the alveolar bone). Gingivitis and periodontatitis are disorders of the gingiva and the deeper periodontal tissues, respectively. Periodontal disease is generally associated with the accumulation of plaque on the teeth. The teeth are coated with a salivary proteinaceous material (pellicle) and thereafter streptococci adhere to this coating. Gingivitis is generally caused by dental plaque, and periodontatitis is caused by the infection spreading to the periodontal pocket or space between the gingival and the tooth root.

Many of the current oral care compositions including toothpastes, mouthwashes, rinses and tooth gels are formulated to clean the oral cavity and kill pathogenic microbes. Such oral care compositions are typically formulated with one or more antimicrobial agents to suppress the microorganisms that contribute both to the initiation and progression of oral malodor, periodontal disease and other undesirable oral conditions. Current oral care compositions comprise antimicrobial agents and are formulated to maximize the kinetics of the antimicrobial agent. The antimicrobial agents are dissolved to provide effective prevention of bad breath, eradication of oral microbes, and penetration, reduction, and elimination of plaque and gingivitis.

One well-known antiseptic agent is thymol, also known as an essential oil, which is utilized for its antimicrobial activity in a range of oral care preparations. In particular, thymol has been utilized in oral hygiene compositions such as mouthwashes in sufficient quantities to provide desired beneficial therapeutic effects. LISTERINE® Brand mouth rinse is a well-known antiseptic mouthwash that has been used by millions of people for over one hundred years and has been proven effective in killing microbes in the oral cavity that are responsible for plaque, gingivitis, and bad breath. Thymol and other essential oils, such as methyl salicylate, menthol, and eucalyptol, are active ingredients (e.g., antimicrobial agents) in antiseptic mouth rinses such as LISTERINE®. Even in small amounts, these essential oils are effective antimicrobial agents. Without being restricted to any specific theory, it is believed that the efficacy and taste of antiseptic mouthwashes such as LISTERINE® may be due to the dissolution and delivery kinetics of these four active agents.

There is still a need to provide efficacious oral care compounds and oral care compositions such as mouthwashes or rinses containing the same having favorable antimicrobial kinetics while exhibiting chemical stability and solubility favorable for efficient delivery and antiseptic effectiveness. There is still a need to provide oral care compositions and compounds that are effective for the prevention or treatment of diseases and conditions of the oral cavity in warm-blooded animals including humans by eliminating or suppressing the presence of pathogenic oral microorganisms responsible for plaque, gingivitis and other undesirable oral conditions in the oral cavity.

SUMMARY OF THE INVENTION

The present invention relates to oral care compositions and methods of using the same for preventing or treating diseases or conditions of the oral cavity in warm-blooded animals including humans. Generally, the oral care composition comprises substituted tropolone compounds in combination with one or more essential oils in amounts effective for suppressing or eliminating the presence of harmful pathogenic oral microorganisms in the oral cavity. The oral care compositions provide a high level of antimicrobial kinetics and efficacy useful for preventing, among others, plaque, gum disease, and oral malodor. In addition, the oral care composition can be formulated into a range of oral care products including, but not limited to, toothpastes, tooth gels, tooth powders, mouthwashes, lozenges, chewing gums, tooth strips, dental floss, orally consumable film and mouth spray.

In one particular aspect of the present invention, there is provided an oral care composition comprising:
(a) an oral care effective amount of at least one compound of Formula

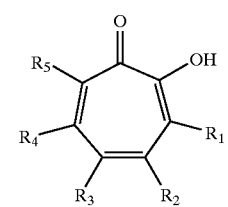

I wherein $R_1$, $R_2$, $R_3$, $R_4$, and $R_5$ are each independently selected from the group consisting of hydrogen, hydroxy, an alkyl group, a hydroxyalkyl group, an alkoxyalkyl group, an alkylene group, an alkenylene group, an alkaryl group, an alkcycloalkyl group, an alkoxy group, an alkenyl group, an alkynyl group, an aryl group, a cycloalkyl group, a cycloalkenyl group, an aliphatic group optionally substituted with 1 to 3 halogens, an aromatic group optionally substituted with 1 to 3 halogens and a carbonyl group, and isomers and pharmaceutically acceptable salts thereof;
(b) at least one essential oil; and
(c) a pharmaceutically acceptable oral carrier.

In a preferred embodiment of the present invention, the oral care composition comprises an oral care effective amount of at least one compound of Formula (I) wherein $R_2$, R3, and $R_5$ are each independently selected from the group consisting of hydrogen, an alkyl group having 1 to 6 carbons, a hydroxyalkyl group having 1 to 6 carbons, and an alkoxyalkyl group wherein the "alkoxy" portion and the "alkyl" portion each have from 1 to 6 carbons, and $R_1$ and $R_4$ are each hydrogen.

Preferably the essential oil is selected from the group consisting of thymol, eucalyptol, menthol, methyl salicylate, and combinations thereof.

In another aspect of the present invention, there is provided a method for preventing or treating diseases or conditions of the oral cavity, comprising administering an oral care effective amount of the oral care composition of the present invention to a warm-blooded animal including humans.

DETAILED DESCRIPTION OF THE INVENTION

The present invention is directed to oral care compositions with antimicrobial efficacy against microorganisms, particularly oral microorganisms responsible for producing undesirable diseases or conditions in the oral cavity, including oral malodor, plaque build-up, and the like, and the resulting tooth and gum diseases that may follow. The oral care compositions may be in a form selected from, for example, mouthwashes, toothpastes, tooth powders, dental creams, dental flosses, liquids, gels, chewing gums, liquid center filled gums, mints, lozenges, orally consumable films and the like. One preferred aspect of the present invention is directed to an oral care composition containing an effective amount of at least one substituted tropolone compound having antimicrobial activity in combination with one or more essential oils. In a particularly preferred aspect of the present invention, there is provided an oral care composition, preferably a mouthwash, containing an effective amount of at least one substituted tropolone compound in combination with at least one essential oil.

Essential oils are volatile aromatic oils which may be synthetic or may be derived from plants by distillation, expression or extraction, and which usually carry the odor or flavor of the plant from which they are obtained. In the oral care composition of the present invention, the essential oils provide antiseptic activity. Some of these essential oils also act as flavoring agents. The essential oils of this invention include but are not limited to thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, lavender oil, mustard oil, phenol, phenyl salicylate, pine oil, pine needle oil, sassafras oil, spike lavender oil, storax, thyme oil, tolu balsam, terpentine oil, clove oil, and combinations thereof. Preferred essential oils are selected from thymol, methyl salicylate, eucalyptol, menthol and combinations thereof.

The present invention is effective for cleaning the oral cavity and/or treating diseases and conditions of the oral cavity including, but not limited to, gingivitis, periodontitis, oral malodor, tooth decay, and the like. The oral care compositions of the present invention provide a high degree of antimicrobial efficacy against microorganisms, particularly pathogenic oral microorganisms, including, but not limited to, *Fusobacterium nucleatum, Prevotella intermedia, Actinomyces viscosus, Campylobacter rectus, Porphyromonas gingivalis, Streptococcus sanguis, Streptococcus mutans*, Actinobacillus, Bacteroides, Capnocytophaga, Eikenella, Propionibacterium, and Candida albicans responsible for oral malodor and build-up of plaque and calculus and the resulting tooth and gum diseases that may follow.

The present invention is also directed to methods of cleaning the oral cavity, and/or treating or preventing diseases or conditions of the oral cavity in warm-blooded animals including humans, by applying to the oral cavity an oral care effective amount of the oral care composition of the present invention.

The term "diseases or conditions of the oral cavity," as used herein, is meant to include diseases of the oral cavity including, but not limited to, periodontal disease, gingivitis, periodontatitis, periodontosis, adult and juvenile periodontatitis, and other inflammatory conditions of the tissues within the oral cavity in warm-blooded animals including humans, plus caries, necrotizing ulcerative gingivitis, and other conditions such as oral malodor or disagreeable mouthfeel. The compositions and methods of treatment and oral care provided by the present invention are particularly effective for preventing or treating periodontal disease (gingivitis and/or periodontatitis) and oral malodor in warm-blooded animals including humans.

In one particular aspect of the present invention, there is provided an oral care composition comprising:

(a) an oral care effective amount of at least one compound of Formula (I)

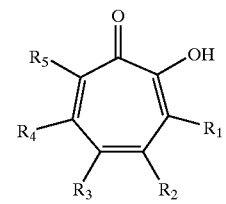

I wherein $R_1$, $R_2$, $R_3$, $R_4$, and $R_5$ are each independently selected from the group consisting of hydrogen, hydroxy, an alkyl group, a hydroxyalkyl group, an alkoxyalkyl group, an alkylene group, an alkenylene group, an alkaryl group, an alkcycloalkyl group, an alkoxy group, an alkenyl group, an alkynyl group, an aryl group, a cycloalkyl group, a cycloalkenyl group, an aliphatic group optionally substituted with 1 to 3 halogens, an aromatic group optionally substituted with 1 to 3 halogens, and a carbonyl group, and isomers and pharmaceutically acceptable salts thereof;

(b) at least one essential oil; and (c) a pharmaceutically acceptable oral carrier.

In a preferred embodiment of the present invention, the oral care composition comprises an oral care effective amount of at least one compound of Formula (I) wherein $R_2$, $R_3$, and $R_5$ are each independently selected from the group consisting of hydrogen, an alkyl group having 1 to 6 carbons, a hydroxyalkyl group having 1 to 6 carbons, and an alkoxyalkyl group wherein the "alkoxy" portion and the "alkyl" portion each have from 1 to 6 carbons, and $R_1$ and $R_4$ are each hydrogen.

Isomers of the compounds of Formula (I) having the desired antimicrobial activity mixtures thereof are included in the scope of the present invention.

In addition, hydrates and solvates with pharmaceutically acceptable organic solvents, as well as prodrugs of the compounds of the present invention are also encompassed by the present invention.

In addition, compounds of Formula (I) or pharmaceutically acceptable salts thereof may be present in the form of addition products with water or various solvents, and these addition products are also included in the scope of the present invention.

The term "pharmaceutically acceptable salts" refers to salts prepared from pharmaceutically acceptable non-toxic bases or acids including inorganic or organic bases and inorganic or organic acids. They can be derived from a variety of organic and inorganic cations well known in the art and include, by way of example, sodium, potassium, calcium, magnesium, ammonium, tetraalkylammonium, and the like, and anions, such as hydrochloride, hydrobromide, tartrate, mesylate, acetate, maleate, oxalate, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. Salts derived from inorganic bases include aluminum, ammonium, calcium, copper, ferric, ferrous, lithium, magnesium, manganic salts, manganous, potassium, sodium, zinc, and the like.

Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Those skilled in the art will recognize a wide variety of non-toxic pharmaceutically acceptable addition salts.

The term "alkyl" refers to monovalent straight and branched alkyl groups preferably having from about 1 to 18 carbon atoms, more preferably from about 1 to 14 carbon atoms, and still more preferably from about 1 to 6 carbon atoms. This term is exemplified by groups such as methyl, ethyl, n-propyl, isopropyl, n-butyl, isobutyl, tert-butyl, n-hexyl, n-octyl, tert-octyl, and the like.

The term "alkylene" refers to divalent alkylene groups preferably having from about 1 to 18 carbon atoms and more preferably from about 1 to 14 carbon atoms which can be straight or branched. The term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "alkenylene" refers to divalent alkenylene groups preferably having from about 2 to 18 carbon atoms and more preferably from about 2 to 14 carbon atoms which can be straight chain or branched and having at least 1 and preferably 1 to 2 sites of alkenyl unsaturation. This term is exemplified by groups such as ethenylene (—CH═CH—), the propenylene isomers (e.g., —CH═$CHCH_2$— and —$C(CH_3)$═CH— and —CH═$C(CH_3)$—) and the like.

The term "alkaryl" refers to -alkylene-aryl groups preferably having from about 1 to 18 carbon atoms in the alkylene moiety and from about 6 to 14 in the aryl moiety. Such alkaryl groups are exemplified by benzyl, phenethyl, and the like.

The term "alkcycloalkyl" refers to -alkylene-cycloalkyl-groups preferably having from about 1 to 18 carbons atoms in the alkylene moiety and from about 3 to 14 in the cycloalkyl moiety. Such alkcycloalkyl groups are exemplified by —$CH_2$—cyclopropyl, —$CH_2$-cyclopentyl, —$CH_2CH_2$-cyclohexyl, and the like.

The term "alkoxy" refers to the group "alkyl-O-". The alkoxy groups include, by way of example, methoxy, ethoxy, n-propoxy, isopropoxy, n-butoxy, tert-butoxy, sec-butoxy, n-pentoxy, and the like, preferably having from about 1 to 6 carbon atoms. The term "alkoxyalkyl" refers to the groups "alkyl-O-alkyl-", preferably the alkyl portion of the group has 1 to 6 carbon atoms and the alkoxy portion of the group has 1 to 6 carbon atoms.

The term "alkenyl" refers to alkenyl groups preferably having from about 2 to 18 and more preferably having from about 2 to 14 carbon atoms and having at least 1 and preferably from 1 to 2 sites of alkenyl unsaturation. Such alkenyl groups are exemplified by ethenyl (—CH═$CH_2$, n-propenyl (—$CH_2CH$═$CH_2$), isopropenyl (—$C(CH_3)$═$CH_2$), and the like.

The term "alkynyl" refers to alkynyl groups preferably having from about 2 to 18 carbon atoms and more preferably from about 2 to 14 carbon atoms and having at least 1 and preferably 1 to 2 sites of alkynyl unsaturation. Such alkynyl groups are exemplified by ethynyl (—CH≡$CH_2$), propargyl (—$CH_2CH$≡$CH_2$) and the like.

The term "aryl" refers to an unsaturated aromatic carbocyclic groups from about 6 to 18 carbon atoms having a single ring (e.g., phenyl) or multiple condensed rings (e.g., naphthyl or anthryl). Examples of aryls include phenyl, naphthyl and the like. Unless otherwise constrained by the definition for the individual substituent, such aryl groups can optionally be substituted with from 1 to 3 substituents selected from the group consisting of alkyl, alkoxy, acyloxy, hydroxy, and the like.

The term "cycloalkyl" refers to cyclic alkyl groups of from about 3 to 18 carbon atoms having a single cyclic ring or multiple condensed rings which can be optionally substituted with from 1 to 3 alkyl groups. Such cycloalkyl groups include, by way of example, cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

The term "cycloalkenyl" refers to cyclic alkenyl groups of from about 4 to 18 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl, and the like.

Preferred tropolone compounds of Formula (I) for use in the oral care compositions of the present invention include those selected from the group consisting of 2-hydroxy-7-methyl-2,4,6-cycloheptatrien-1-one; 2-hydroxy-7-heptyl-2,4,6-cycloheptatrien-1-one; 2-hydroxy-7-(methoxymethyl)-2,4,6-cycloheptatrien-1-one; 2-hydroxy-4-methyl-2,4,6-cycloheptatrien-1-one; 2-hydroxy-4-dimethyl-2,4,6-cycloheptatrien-1-one; and 2-hydroxy-7-(hexloxymethyl)-2,4,6-cycloheptatrien-1-one, and combinations thereof.

It will be understood that some of the above compounds may exist in the form of salts. In such cases, the compounds may be ionized and accompanied by a pharmaceutically acceptable anion or cation as appropriate. Most commonly, a cation is a monovalent material such as sodium, potassium or ammonium, but it can also be a multivalent cation in combination with a pharmaceutically acceptable monovalent anion, for example calcium with a chloride, bromide, iodide, hydroxyl, nitrate, sulfonate, acetate, tartate, oxalate, succinate, palmoate, or the like anion; magnesium with such anions; zinc with such anions or the like.

The term "oral care composition" is meant to include products, which are retained in the oral cavity for a sufficient time to contact the dental surfaces and/or oral mucosal tissues and exhibit the desired oral activity. The term "oral care effective amount" as used herein is meant to be an amount of at least one tropolone compound, sufficient to prevent or treat diseases or conditions of the oral cavity, or to significantly eliminate or at least suppress the presence of undesirable microorganisms in the oral cavity, without causing side effects within the scope of sound medical and dental judgment. The oral care effective amount of the tropolone compounds of the present invention may vary with the particular condition (e.g., to treat disease of the oral cavity or malodor) being treated, the age and physical condition of the patient being treated, the severity of the condition, the duration of treatment, the nature of concurrent therapy, the specific form (i.e., salt) of the tropolone compound employed, and the particular carrier from which the tropolone compound is applied.

The concentration of the tropolone compounds in the oral care composition of the present invention depends on the type of composition (e.g., toothpaste, mouthwash and rinse, lozenge, gum, etc.) used to apply the tropolone compounds to the gingival/mucosal tissue and/or teeth, due to differences in efficiency of the compositions contacting the tissue and teeth and due also to the amount of the composition generally used. The concentration may also depend on the diseases or conditions being treated.

In a preferred embodiment, the oral care compositions of the present invention can include from about 0.001% to 10.0% by weight based on the total weight of the oral care composition, preferably from about 0.01% to 5.0% by weight, and more preferably from about 0.1% to 2.0% by weight of the tropolone compounds of the present invention with the remainder of the formulation being the essential oils, the carrier and other materials known in the art as oral care composition components. Such additional components may include buffers, surfactants, solubilizers, preservatives, emulsifying agents, isotonizers, stabilizers, pH adjusting agents, sweeteners, coloring agents, and the like.

The oral care composition of the present invention contains an antimicrobial effective amount of an antimicrobial compound having a structure of Formula (I) in combination with one or more antimicrobially-effective essential oils as the active components. Such antimicrobially-effective essential oils may include thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, lavender oil, mustard oil, phenol, phenyl salicylate, pine oil, pine needle oil, sassafras oil, spike lavender oil, storax, thyme oil, tolu balsam, terpentine oil, clove oil and the like. The composition generally takes the form of a solution containing these components in water.

The admixture of the antimicrobial compounds of Formula (I) and antimicrobial essential oils preferably those selected from the group consisting of thymol, menthol, eucalyptol, methyl salicylate, and combinations thereof, provides a synergistic antimicrobial effect.

In the oral care compositions, the essential oils are used in amounts effective to provide oral care including the elimination or suppression of oral microorganisms in the oral cavity. Generally, the essential oils may be in the oral care composition of the present invention in an amount of from about 0.001% to 8.0% by weight based on the total weight of the composition; preferably in an amount of from about 0.004% to 3.0% by weight; and more preferably in an amount of from about 0.007% to 2.0% by weight. Amounts employed in the oral care compositions may vary depending on the form of the composition may be readily ascertained by those skilled in the art. The compositions of the present invention generally contain thymol and/or one or more other essential oils. Preferably, the additional essential oils are eucalyptol, menthol, or methyl salicylate, or mixtures thereof. Most preferably, the composition contains all four of these essential oils.

Thymol (($CH_3$)$_2$CHC$_6$H$_3$(CH$_3$)OH; isopropyl-m-cresol), also known by the chemical formula 5-methyl 2-(1-methylethyl) phenol, is an effective antimicrobial agent, and is typically obtained from the essential oil of Thymus vulgaris Labiatae and Monarda punctata Labiatae. Thymol is a white crystalline powder with an aromatic odor and taste and is soluble in organic solvents but only slightly soluble in deionized water. Thymol may be in the oral care composition of this invention in an amount of from about 0.001% to 2.0% by weight based on the total weight of the composition; preferably in an amount of from about 0.01% to 0.6% by weight; and more preferably in an amount of from about 0.02% to 0.5% by weight.

Menthol ($CH_3C_6H_9(C_3H_7)$OH; hexylhydroxythymol) also possesses antiseptic properties and provides a cooling, tingling sensation. Menthol is isolated principally from the oil of Mentha arvensis. In its commercial form, menthol is available as L-menthol crystals obtained from a process involving cooling of the oil. Fractional distillation of peppermint oil, which usually contains from about 40% to about 65% menthol represents another important source of menthol. Synthetic sources of L-menthol are also available. Menthol may be in the oral care composition of the present invention in an amount of from about 0.001% to 2.0% by weight based on the total weight of the composition; preferably in an amount of from about 0.01% to 0.7% by weight; and more preferably in an amount of from about 0.01% to 0.6% by weight.

Eucalyptol ($C_{10}H_{18}O$; cineol), another essential oil with antiseptic properties, is derived from the eucalyptus tree. Eucalyptol is a terpene ether that provides a cooling, spicy taste and antiseptic activity. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels. Eucalyptol may be in the oral care composition of the present invention in an amount of from about 0.001% to 2.0% by weight based on the total weight of the composition; preferably in an amount of from 0.005% to 0.5% by weight; and more preferably in an amount of from about 0.007% to 0.4% by weight.

Methyl salicylate ($C_6H_4OHCOOCH_3$), also known as wintergreen oil, is the main ingredient in many essential oils, constituting about 99% of oil of wintergreen (Gaultheria procumbens) and sweet birch (Betula lenta). Methyl salicylate, which has a distinctive refreshing aroma, is used widely in mouthwashes, chewing gums and other oral and pharmaceutical preparations. Methyl salycylate is capable of providing flavoring and organoleptic flavor tones to the oral care composition together in addition to its antimicrobial function. Methyl salycylate may be in the oral care composition of the present invention in an amount of from about 0.001% to 2.0% by weight based on the total weight of the composition; preferably in an amount of from about 0.004% to 0.6% by weight; and more preferably in an amount of from about 0.01% to 0.6% by weight.

The oral care composition of the present invention may contain the following essential oils in percentages by weight based on the total weight of the oral care composition: (a) thymol from about 0.001% to 2.0% by weight; (b) menthol from about 0.001% to 2.0% by weight; (c) eucalyptol from about 0.001% to 2.0% by weight; and (d) methyl salicylate from about 0.001% to 2.0% by weight.

In a preferred embodiment of the oral care composition of the present invention, the oral care composition may contain the following essential oils in percentages by weight based on the total weight of the oral care composition: (a) thymol from about 0.01% to 0.6% by weight; (b) menthol from about 0.01% to 0.7% by weight; (c) eucalyptol from about 0.005% to 0.5% by weight; and (d) methyl salicylate from about 0.004% to 0.6% by weight.

In a more preferred embodiment of the oral care composition of the present invention, the oral care composition may contain the following essential oils in percentages by weight based on the total weight of the oral care composition: (a) thymol from about 0.02% to 0.5% by weight; (b) menthol from about 0.01% to 0.6% by weight; (c) eucalyptol from about 0.007% to 0.4% by weight; and (d) methyl salicylate from about 0.01% to 0.6% by weight.

The oral care compositions of the present invention containing tropolone compounds of Formula (I), and thymol and/or at least one other essential oil provides effective antimicrobial activity. The oral care compositions may further comprise other antimicrobial agents if desired. Such exemplary antimicrobial agents include chlorhexidine, chitosan, triclosan, cetylpyridiumchloride, domiphen bromide, and the like. The amount of such antimicrobial agents employed in the composition of this invention can be readily determined by those skilled in the art. The carrier for the oral care compositions of the present invention, and particularly for the essential oils containing compositions, may be aqueous medium. The aqueous medium may be a water-alcohol mixture, generally a water-ethanol or water-1-propanol mixture. The ethanol content level can be from about 0.01% to 70% by weight based on the total weight of the composition to solubilize and deliver the antimicrobial agents and to provide a clear, aesthetically attractive liquid medium. A favorable amount of ethanol for enhancement of the organoleptic cues of the oral care compositions, specifically mouthwash compositions, may range from about 0.1% to 30% by weight, more preferably from about 20% to 30% weight, although lesser amounts may be used if desired. Alternatively, the aqueous medium is water.

The oral care compositions may be selected, for example, from the group consisting of mouthwashes or rinses, toothpastes, tooth powders, dental creams, dental flosses, liquids, gels, chewing gums, liquid center filled gums, mints, lozenges, oral film forming dentifrices, orally consumable films and the like.

The oral care compositions of the present invention comprise a pharmaceutically acceptable oral carrier, in an amount appropriate to accommodate the other components of the formulation. The term "pharmaceutically acceptable oral carrier" refers to a vehicle capable of being mixed with the active components for delivery to the intended target in an oral cavity, and which will not cause harm to warm-blooded animals including humans. The oral carriers further include those components of the composition that are capable of being commingled without interaction in a manner which would substantially reduce the composition's stability and/or efficacy for oral care including preventing or treating diseases or conditions of the oral cavity in warm-blooded animals including humans, in accordance with the compositions and methods of the present invention.

The pharmaceutically acceptable oral carriers of the oral care compositions can include one or more compatible solid or liquid filler diluents or encapsulating substances, which are suitable for oral administration. The carriers or excipients of the present invention may be in any form appropriate to the mode of delivery, for example, solutions, colloidal dispersions, emulsions, suspensions, rinses, gels, foams, powders, solids, and the like, and can include the usual and conventional components of toothpastes (including gels and gels for subgingivial application), mouthwashes and rinses, mouth sprays, chewing gums, orally consumable films and lozenges (including breath mints). Carriers suitable for the preparation of compositions of the present invention are well known in the art. Their selection will depend on secondary considerations like taste cost, and shelf stability, etc.

Types of carriers which may be included in the oral compositions of the present invention are abrasives, fluoride ions, thickening agents, humectants, flavoring and sweetening agents, anticalculus agents, alkali metal bicarbonate salts, surfactants including nonionic and amphoteric surfactants, and anionic surfactants, and miscellaneous carriers such as water, titanium dioxide, anti-inflammatory gents, and the like.

Preferred compositions of the present invention are mouthwashes, rinses, and mouth sprays. Components of such mouthwashes, rinses and mouth sprays typically include water being present in an amount of from about 45% to 95% by weight, and one or more of ethanol up to 70%, a humectant up to 50%, a surfactant from about 0.01% to 7%, a flavoring agent from about 0.04% to 2%, a sweetening agent from about 0.1% to 3%, and a coloring agent from about 0.001% to 0.5%. Such mouthwashes, rinses and mouth sprays may also include one or more of an anticaries agent from about 0.05% to 0.3% (e.g., fluoride ion), and an anticalculus agent from about 0.1% to 3%.

Other preferred compositions of the present invention are dental solutions. Components of such dental solutions generally include water from about 90% to 99% by weight based on the total weight of the oral care composition, and one or more of a preservative from about 0.01% to 0.5%, a thickening agent up to 5%, a flavoring agent from about 0.1% to 3%, and a surfactant up to 5%.

Other preferred compositions of the present invention are orally consumable films or thin strips. Orally consumable films typically comprise a rapidly dissolvable non-self-adhering polymer-based thin film vehicle. Such compositions are typically administered to the oral cavity where they rapidly dissolve upon contact with saliva and provide rapid delivery of the active ingredients. LISTERINE® POCKET- PAKS™ brand oral care strip products made by PFIZER, Inc. of Morris Plains, N.J. are perhaps the most successful examples of an edible film compositions effective in delivering therapeutic agents particularly antimicrobial agents in the form of LISTERINE® essential oils to the oral cavity. Components of such compositions generally include water in an amount up to 75% by weight, a water soluble film forming polymer including, but not limited to, pullulan, in an amount of up to 25%, a flavoring agent in an amount of from about 0.01% to 10%, a surfactant in an amount up to 5%, and optionally, copper salts in an amount of from about 0.01% to 5%.

Other preferred compositions of the present invention are in the form of dentifrices such as toothpastes, tooth gels, and tooth powders. Components of such toothpaste, and tooth gels generally include one or more of a dental abrasive, generally from about 10% to 50% by weight, a surfactant such as anionic, nonionic, or zwitterionic detergent from about 0.5% to 10%, a thickening agent from about 0.1% to 5%, a humectant from about 10% to 55%, a flavoring agent from about 0.04% to 2%, a sweetening agent from about 0.1% to 3%, a coloring agent from 0.01% to 0.5%, and water from about 2% to 45%. Such toothpastes or tooth gels may also include one or more of an anticaries agent from about 0.05% to 0.3% (e.g., fluoride ion), and an anticalculus agent from about 0.1% to 13%. The liquids and solids are proportioned to form a creamy or gelled mass, which is extrudable from a pressurized container or from a collapsible tube. Tooth powders, of course, contain substantially all non-liquid components.

Other preferred compositions of the present invention are in the form of microcaps or more commonly known as gel beads, which generally comprise a flavorant in an amount of from about 0.1% to 10% by weight, a lipophilic filler in an amount of from about 1% to 60%, an emulsifier in an amount of from about 0.1% to 5% and a sweetening agent in an amount of from about 0.01% to 3%.

Chewing gum compositions typically include one or more of gum base from about 50% to 99% by weight, a flavoring agent from about 0.4% to 2% and a sweetening agent from about 0.01% to 5%.

The term "lozenge" as used herein includes: breath mints, troches, pastilles, microcapsules, and fast-dissolving solid forms including freeze dried forms (cakes, wafers, thin films, and tablets) and fast dissolving solid forms including compressed tablets. The term "fast dissolving solid form" as used herein means that the solid dosage form dissolves in less than about 60 seconds, preferably less than about 15 seconds, more preferably less than about 5 seconds, after placing the solid dosage form in the oral cavity. Lozenges include discoid shaped solids comprising a therapeutic agent in a flavored base. The base may be a hard sugar candy, glycerinated gelatin, or combination of sugar with sufficient mucilage to give it form. Lozenge compositions (compressed tablet type) typically include one or more fillers compressible sugar), flavoring agents and lubricants.

Surface active agents (surfactants) can be employed in the composition of the present invention. They are organic materials which aid in the complete dispersion of the components including the active agents and flavoring oils throughout the solution as well as dispersing the preparation throughout the oral cavity and enable the compositions to provide a clear, uniform appearance that is aesthetically more appealing. Preferably, the surfactant used in the compositions of the present invention is a non-ionic surfactant or anionic surfactant employed in an amount sufficient to help solubilize the active components. By sufficient amount it is meant that the surfactant is present in an amount that effectively assists in the solubilization and delivery system kinetics of the tropolone compounds and the essential oils.

Additional components may be added as known by those skilled in the art. For example, acidic preservatives such as sorbic or benzoic acid may be added to reduce pH levels. Buffer systems may be necessary to control the pH of the composition at optimal levels. This is generally accomplished through the addition of a weak acid and its salt or a weak base and its salt. Useful systems have been found to be sodium benzoate and benzoic acid in amounts of from about 0.01% to 4.0% by weight, and sodium citrate and citric acid in amounts of from about 0.001% to 0.2% by weight. Preferably, the buffers are incorporated in amounts that maintain the pH at levels of from about 3.5 to 9.0, and more preferably from about 4.0 to 7.0.

In another embodiment of the present invention, there is provided a method of treating or preventing diseases or conditions of the oral cavity in warm-blooded animals including humans, by applying an oral care effective amount of the oral care composition of the present invention to the oral cavity. The oral care effective amount of the oral care compositions of the present invention is preferably applied to the mucosal tissue of the oral cavity, to the gingival tissue of the oral cavity, and/or surface of the teeth, for the treatment or prevention of the above-mentioned diseases or conditions of the oral cavity, in one or more conventional ways. For example, the gingival or mucosal tissue may be rinsed with a solution (e.g., mouthwash, rinse) containing the composition of the present invention; if a dentifrice (e.g., toothpaste, tooth gel, or tooth powder) is employed, the gingival/mucosal tissue or teeth may be bathed in the liquid and/or lather generated by brushing the teeth; etc., for a sufficient time, preferably from about 10 seconds to 10 minutes, more preferably from about 30 seconds to 60 seconds.

The method of the present invention generally further involves expectoration of most of the composition following such contact. The frequency of such contact is preferably from about once a week to about four times per day, more preferably from about 3 times per week to three times per day, even more preferably once per day to twice per day. The period of such treatment typically ranges from about one day to a lifetime. For particular diseases or conditions of the oral cavity the duration of treatment depends on the severity of the oral disease or condition being treated, the particular delivery form utilized and the patient's response to treatment. If the delivery to the periodontal pockets is desirable, such as with the treatment of periodontal disease, a mouthwash or rinse can be delivered to the periodontal pocket using a syringe or a water injection device, for example. After irrigating, the subject can swish the wash in the mouth to also cover the dorsal portion of the tongue and other gingival/mucosal surfaces. In addition to toothpaste, non-abrasive gel, tooth gel, etc., can be brushed onto the tongue surface and other gingival and mucosal tissues of the oral cavity.

Other non-limiting examples include chewing gum that contains the composition of the present invention, chewing or sucking on a breath tablet or lozenge. Preferred methods of applying the oral care compositions of the present invention to the gingival/mucosal tissue and/or teeth include rinsing with a mouthwash or rinse solution and brushing with a dentifrice. Other methods of applying the present composition to the gingival/mucosal tissue and surfaces of the teeth are apparent to those skilled in the art.

The present substituted tropolone compounds of Formula (I) employed in the present invention may be prepared from readily available starting materials using the following general methods and procedures. It will be understood that where typical or preferred process conditions (i.e. reaction temperatures, times, mole ratios of reactants, solvents, pressures, etc.) are given, other process conditions may also be used unless otherwise stated. Optimum reaction conditions may vary with the particular reactants or solvents used, however such reaction conditions may be determined by one of ordinary skill in the art through routine optimization procedures.

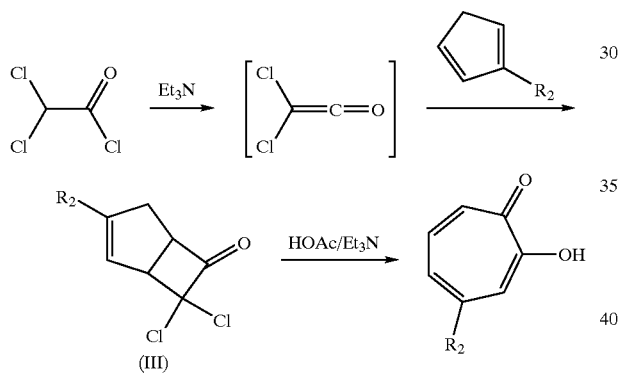

Scheme 1

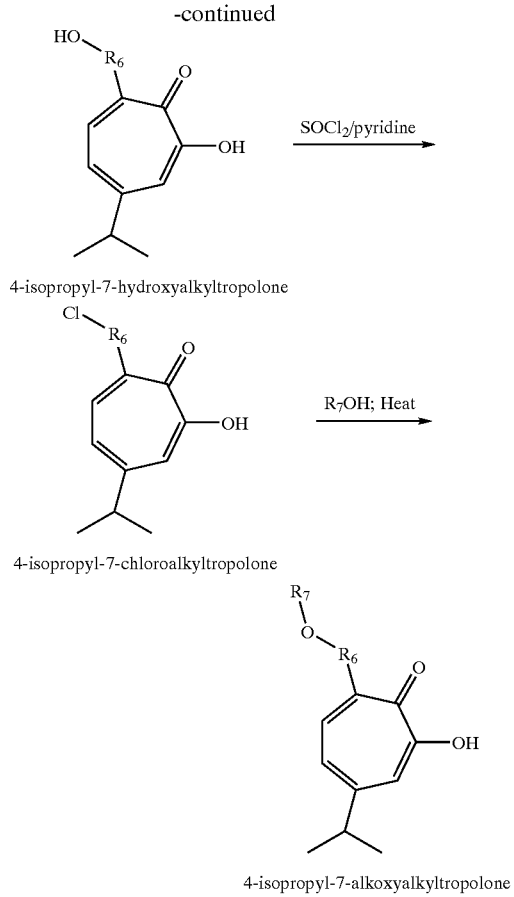

Compounds of Formula (I) can be prepared as shown in Scheme 1 by reacting dichloroacetyl chloride with an $R_2$-substituted cyclopentadiene compound in the presence of a base such as triethylamine to yield a cycloadduct of Formula (III). The cycloadduct of Formula (III) is then treated with an acid such as acetic acid and a base such as triethylamine to yield the final desired product, a 4-alkyltropolone compound. When $R_2$ is isopropyl the resulting compound is hinokitiol which is used as a starting material in Scheme 2.

Compounds of Formula (I) can further be prepared as shown in Scheme 2 by treating hinokitiol with a carbonyl compound ($R_6$=O, wherein $R_6$ is an alkyl group) such as formaldehyde, acetaldehyde, proprionaldehyde, butyraldehyde, and the like, in the presence of a base such as potassium hydroxide, and thereafter adding an acid such as hydrochloric acid to yield a 4-isopropyl-7-hydroxyalkyltropolone compound. The 4-isopropyl-7-hydroxyalkyltropolone compound is then treated with a chlorinating agent such as $SOCl_2$ in the presence of a base such as pyridine to yield a 4-isopropyl-7-chloroalkyltropolone compound. The 4-isopropyl-7-chloroalkyltropolone compound is reacted with an alcohol ($R_7OH$; wherein $R_7$ is an alkyl group) such as methanol, ethanol, propanol, and the like, in the presence of heat to yield the corresponding a 4-isopropyl-7-alkoxyalkyltropolone compound.

Scheme 3

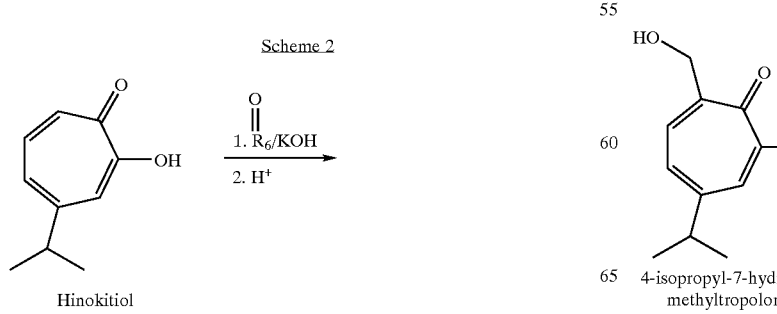

4-isopropyl-7-hydroxy-methyltropolone

EXAMPLE 1

Mouthwash Composition Containing Compounds of Formula (I) and Essential Oils A mouthwash composition was prepared having the following components shown below in Table 1.

TABLE 1

| Components | % by weight |
| --- | --- |
| 1) Thymol | 0.064 |
| 2) Eucalyptol | 0.092 |
| 3) Methyl Salicylate | 0.060 |
| 4) Menthol | 0.042 |
| 5) Alcohol, USP | 21.6 |
| 6) Compound of Formula (I) | 0.03 |
| 7) Flavoring Oil | 0.085 |
| 8) Poloxamer 407 | 0.15 |
| 9) Benzoic Acid | 0.15 |
| 10) Sorbitol | 20 |
| 11) Saccharin | 0.117 |
| 12) FD & C Green #3 | 0.0005 |
| 13) n-Propanol | 0.5 |
| 14) Water, USP | QS to 100 |

The composition was prepared by adding the essential oils (thymol, menthol, methyl salicylate and eucalyptol) and the compound of Formula (I), flavoring oils, poloxamer 407 and benzoic acid to alcohol followed by addition of 250 ml of water. Sorbitol, saccharin, and the dye were added to the resulting mixture followed by the addition of water to provide a 1000 ml sample of the mouthwash composition.

EXAMPLE 2

Scheme A

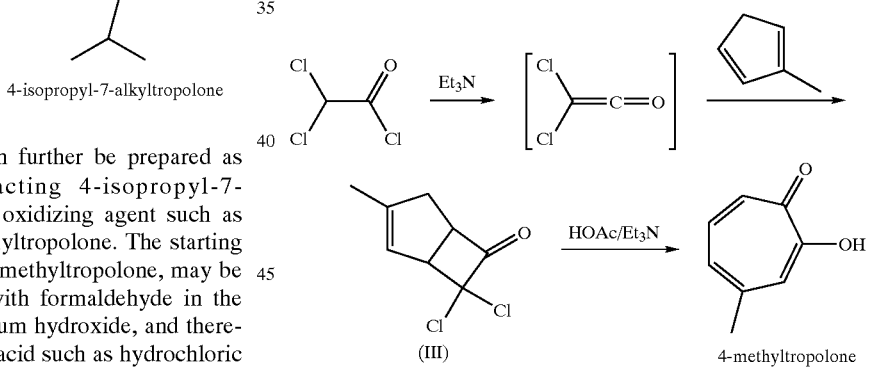

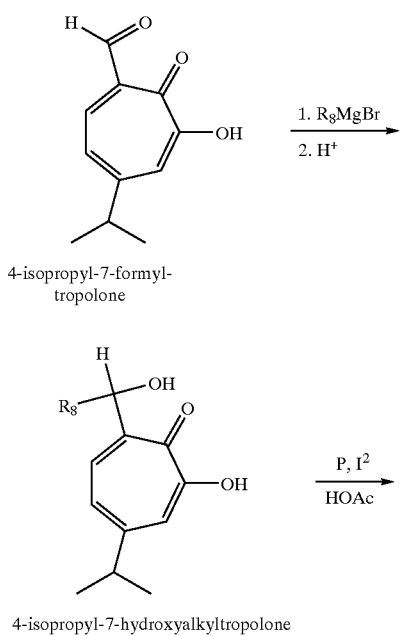

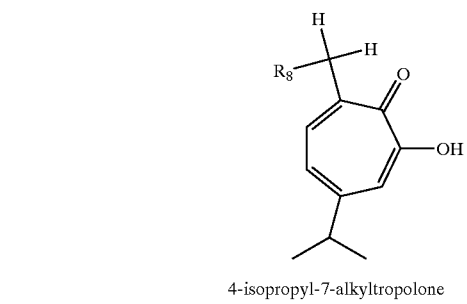

Compounds of Formula (I) can further be prepared as shown in Scheme 3 by reacting 4-isopropyl-7-hydroxymethyltropolone with an oxidizing agent such as $MnO_2$ to yield 4-isopropyl-7-formyltropolone. The starting compound, 4-isopropyl-7-hydroxymethyltropolone, may be prepared by reacting hinokitiol with formaldehyde in the presence of a base such as potassium hydroxide, and thereafter treating the reaction with an acid such as hydrochloric acid. 4-isopropyl-7-formyltropolone is reacted with an alkylmagnesium bromide compound ($R_8MgBr$; wherein $R_8$ is an alkyl group) and the reaction is quenched with an acid such as hydrochloric acid to yield a 4-isopropyl-7-hydroxyalkyltropolone compound. The 4-isopropyl-7-hydroxyalkyl-tropolone compound is treated with a reducing agent such as phosphorus, preferably red phosphorus, in the presence of an acid such as acetic acid, whereupon as oxidizing agent such as iodine is added to the reaction to yield a final product of a 4-isopropyl-7-alkyltropolone compound.

The following examples are offered only to illustrate the invention, and should not be interpreted as a limitation thereon. For example, optimum reaction conditions may vary with the particular reactants or solvents used, however such reaction conditions may be determined by one of ordinary skill in the art through routine optimization procedures.

As illustrated in Scheme A, a solution comprising 25 mL of triethylamine and 100 mL of a mixture of hexanes was added dropwise to a solution containing 48.5 g of methylcyclopentadiene (prepared from cracking methylcyclopentadiene dimer) and 22.5 g of dichloroacetyl chloride in 200 mL of a mixture of hexanes at 0° C. The mixture was stirred for about one hour and thereafter poured into 150 mL of water at about 0° C. The layers were separated and the aqueous phase was extracted with two 75 mL portions of hexanes. The combined organic layers were washed twice with water, then dried over $Na_2SO_4$ and concentrated to yield an oil. Fractional distillation was performed under vacuum to yield a cycloadduct of Formula (III), which was dissolved in 80 mL of acetone. The resulting solution was then added to a solution containing 28.5 mL of acetic acid, 82.5 mL of triethylamine, 36 mL of water and 100 mL of acetone. The mixture was refluxed under nitrogen for about four hours. The acetone was removed from the mixture under reduced pressure. An additional 100 mL of water was added and then the solution was extracted three times each with 100 mL portions of ether. The combined organic extracts were washed with water and dried over $MgSO_4$. The final product, 4-methyltropolone, was recrystallized from hexanes to yield a white solid.

EXAMPLE 3

Synthesis of 4-isopropyl-7-methoxymethyltropolone

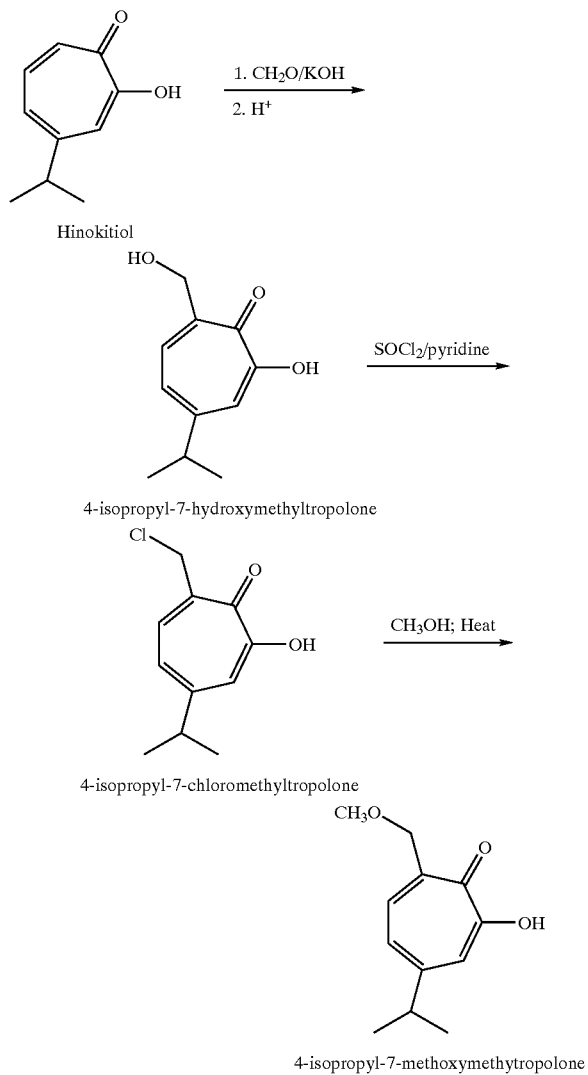

As illustrated in Scheme B, a solution comprising 10 g of hinokitiol and 18.8 mL of 25% aqueous KOH was heated to 60° C. under argon. Formaldehyde was added in 1 mL portions every 30 minutes until a total of 10 mL was added. The reaction mixture was concentrated to a yellow paste and 300 mL of acetone was added. The resulting yellow solid was collected and washed with acetone. The solid was suspended in 250 mL in dichloromethane and 50 mL of 2.0M HCl was added. The aqueous layer was washed with dichloromethane and the combined organic layers were washed with water, and then dried over $Na_2SO_4$. The solvent was removed under vacuum leaving an oil which solidified upon trituration with petroleum ether. An ice cold solution of 4.0 g of 4-isopropyl-7-hydroxymethyltropolone and 1.8 mL of pyridine in 100 mL of diethyl ether was vigorously stirred for two hours as a solution of $SOCl_2$ (2.5 mL) in 80 mL of ether was added thereto. The resulting mixture was concentrated to yield a solid. Boiling petroleum ether was added to the solid. The resulting mixture was filtered and the filtrate was cooled to yield 4-isopropyl-7-chloromethyltropolone in the form of a solid. The solid product was then refluxed in methanol under nitrogen for about two hours and then concentrated to yield a golden oil. A stream of $N_2$ gas was passed over the oil until it solidified to yield 4-isopropyl-7-methoxymethyltropolone in the form of a pale yellow solid.

EXAMPLE 4

Synthesis of 4-Isopropyl-7-hexyltropolone

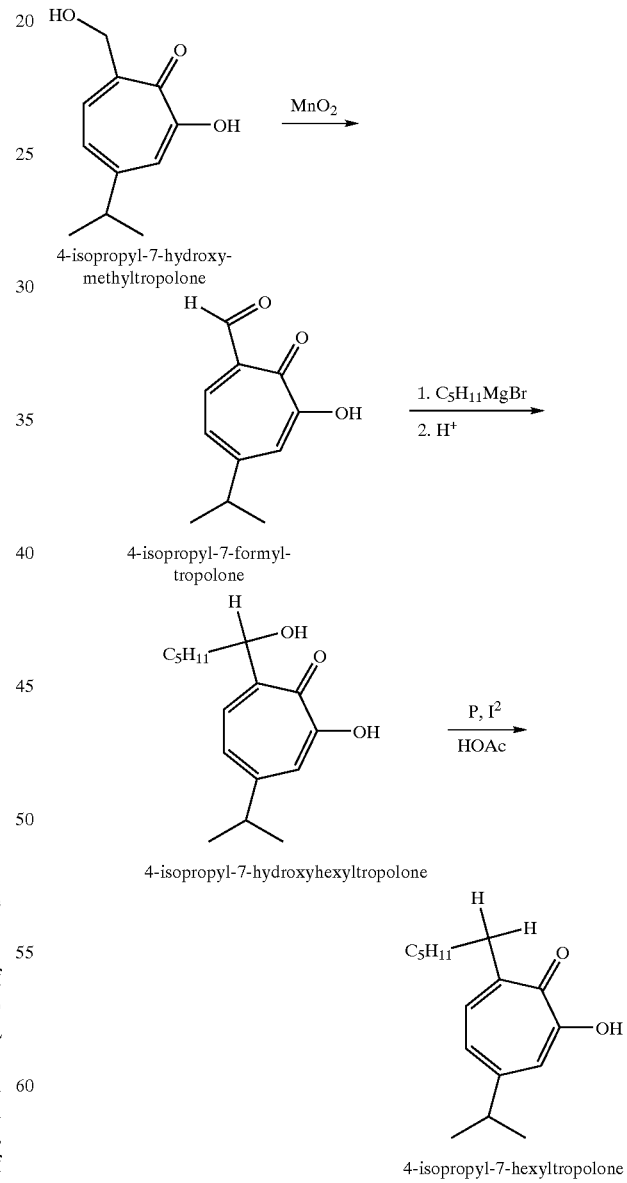

As illustrated in Scheme C, 4-isopropyl-7-methoxymethyltropolone as produced in Example 2 was oxidized in the presence of MnO$_2$ to yield 0.85 g of 4-isopropyl-7-formyltropolone. 4-isopropyl-7-formyltropolone was added to ether to yield a solution, which was stirred under N$_2$ at 0° C. 5 mL of a 2.0 M solution of pentylmagnesium bromide was added to the solution via a syringe. The mixture was stirred for about 45 minutes and then quenched with 20 mL of water. 10 mL of 0.5 M HCl and 100 mL of ether was added to the mixture. The layers were separated and the organic layer was dried over Na$_2$SO$_4$. The solvent was removed and the resulting oil was triturated with petroleum ether to yield 4-isopropyl-7-hydroxyhexyltropolone in the form of a yellow oil. The oil product was mixed in 2 mL of water, 1 g of red phosphorus and 15 mL of acetic acid. The mixture was stirred well and 1 g of I$_2$ was added. The reaction mixture was refluxed for about an hour, and thereafter filtered. 150 mL of water was added the filtrate. K$_2$CO$_3$ was added to the mixture to generate a basic pH. The mixture was extracted with petroleum ether. The organic layer was washed with Na$_2$S$_2$O$_3$ and then with water, and was dried over Na$_2$SO$_4$ to yield 4-isopropyl-7-hexyltropolone in the form of an oil.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. An oral care composition comprising an oral care effective amount of:
   a) a tropolone compound selected from the group consisting of methyl-7-hydroxymethyltropolone, 4-methyl-7-methoxymethyltropolone, 4,7-dimethyltropolone, 7-methyl-4-isopropyltropolone, 7-hiexyl-4-isopropyltropolone, 4-t-butyltropolone, 5-t-butyltropolone, 4-methyltropolorie, 7-methoxyrnethyl-4-isopropyltropolone, 7-hexloxymethyl-4-isopropyltropolone and combinations thereof;
   b) at least one essential oil, and
   c) a pharmaceutically acceptable oral carrier.

2. The oral care composition of claim 1 wherein the oral effective amount of the tropolone compound is from about 0.001% to 10% by weight based on the total weight of the oral care composition.

3. The oral care composition of claim 2 wherein the oral effective amount of the tropolone compound is from about 0.01% to 5.0% by weight.

4. The oral care composition of claim 3 wherein the oral effective amount of the tropolone compound is from about 0. 1% to 2.0% by weight.

5. The oral care composition of claim 1 wherein the at least one essential oil selected from the group consisting of thymol, menthol, methyl salicylate (wintergreen oil), eucalyptol, carvacrol, camphor, anethole, carvone, eugenol, isoeugenol, limonene, losimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, gualacol, lavender oil, mustard oil, phenol, phenyl salicylate, pine oil, pine needle oil, sassafras oil, spike lavender oil, storax, thyme oil, tolu balsam, terpentine oil, clove oil and combinations thereof.

6. The oral care composition of claim 5 wherein the at least one essential oil selected from the group consisting of thymol, eucalyptol, menthol, and methyl salicylate.

7. The oral care composition of claim 6 wherein the oral care effective amount of thymol is from about 0.001% to 2.0% by weight based on the total weight of the oral care composition.

8. The oral care composition of claim 7 wherein the oral care effective amount of thymol is from about 0.01%, to 0.6% by weight.

9. The oral care compositions of claim 8 wherein the oral care effective amount of thymol is from about 0.02% to 0.5%, by weight.

10. The oral care composition of claim 1 wherein the oral care effective amount of at least one essential oil is from about 0.001% to 8.0% by weight based on the total weight of the oral care composition.

11. The oral care composition of claim 6 wherein the oral care effective amount of the at least one essential oil comprises 0.064% by weight of thymol, 0.092% by weight of eucalyptol, 0.060% by weight of methyl salicylate, and 0.042% by weight of menthol, each based on the total weight of the oral care composition.

12. The oral care composition of claim 1 further comprising an alcohol in an amount of from about 0.01% to 70% by weight based on the total weight of the oral care composition.

13. The oral care composition of claim 12 wherein the amount of alcohol is from about 0.1% to 30% by weight.

14. The oral care composition of claim 13 wherein the alcohol is ethanol.

15. The oral care composition of claim 6 wherein the oral care effective amount of the tropolone compound is from about 0.03% to 2% by weight based on the total weight of the oral care composition, and of the at least one essential oil is 0.064% by weight of thymol, 0.092% by weight of eucalyptol, 0.060% by weight of methyl salicylate, and 0.042% by weight of menthol, each based on the total weight of the oral care composition.

16. The oral care composition of claim 1 wherein the amount of the at least one essential oil is from about 0.001% to 8% by weight based on the total weight of the oral care composition.

17. A method for treating or preventing diseases or conditions of the oral cavity in warm-blooded animals including humans, comprising applying an oral care effective amount of the composition of claim 1 to the oral cavity.

18. The method of claim 17 comprising applying the composition of claim 1 in a form selected from the group consisting of toothpastes, mouthwashes, gels, tooth powders, film forming dentifrices, chewing gums, mouth sprays and lozenges.

19. The method of claim 18 comprising applying the composition of claim 1 in the form of a mouthwash.

20. The oral care composition of claim 1 in a form selected from the group consisting of toothpaste, mouthwashes, gels, toothpowders, film forming dentifrices, chewing gums, mouth sprays and lozengers.

21. The oral care composition of claim 20 wherein the oral care composition is in the form of a mouthwash.

* * * * *

UNITED STATES PATENT AND TRADEMARK OFFICE
CERTIFICATE OF CORRECTION

PATENT NO. : 6,689,342 B1
DATED : February 10, 2004
INVENTOR(S) : Pan, Pauline

It is certified that error appears in the above-identified patent and that said Letters Patent is hereby corrected as shown below:

Column 3,
Line 47, the word "linalaol" should read -- linalool --
Line 55, the word "clove oil" is redundant and should be removed.

Column 7,
Line 60, the word "linalaol" should read -- linalool --

Column 8,
Line 1, the word "clove oil" is redundant and should be removed.

Column 19,
Line 36, the word "hiexyl" should read -- hexyl --
Line 57, the word "losimen" should read -- osimen --
Line 59, the word "linalaol" should read -- linalool --
Line 65, the word "gualacol" should read -- guaiacol --

Column 20,
Line 3, the word "clove oil" is redundant and should be removed.
Lines 44-46, Claim 16 is a duplicate of claim 10 and should be reomoved.

Signed and Sealed this

Sixth Day of July, 2004

JON W. DUDAS
*Acting Director of the United States Patent and Trademark Office*